United States Patent [19]
Ordino et al.

[11] Patent Number: 6,162,421
[45] Date of Patent: Dec. 19, 2000

[54] PIGMENTED WATER-IN-OIL EMULSION COSMETIC STICKS

[75] Inventors: Renee Joan Ordino, Lakewood, N.J.; Natividad Jose, Jamaica, N.Y.; Robert Walter Sandewicz, Spotswood; Ann Marshall Ureneck, Red Bank, both of N.J.

[73] Assignee: Revlon Consumer Products Corporation, New York, N.Y.

[21] Appl. No.: 09/186,554

[22] Filed: Nov. 5, 1998

Related U.S. Application Data

[60] Provisional application No. 60/065,880, Nov. 17, 1997.

[51] Int. Cl.$^7$ ............................. A61K 7/027; A61K 9/107
[52] U.S. Cl. .............................. 424/64; 424/63; 424/401; 424/DIG. 5; 424/78.03; 514/63; 514/938
[58] Field of Search ................................. 424/63, 64, 401, 424/DIG. 5, 78.03; 514/63, 938

[56] References Cited

U.S. PATENT DOCUMENTS

| | | | |
|---|---|---|---|
| 5,310,547 | 5/1994 | Dunphy | 424/64 |
| 5,342,134 | 8/1994 | Lombardi | 401/78 |
| 5,446,457 | 11/1995 | Schneider | 424/401 |
| 5,725,845 | 3/1998 | Krog | 424/64 |
| 5,800,816 | 9/1998 | Brieva | 424/63 |
| 5,849,275 | 12/1998 | Calello et al. | 424/64 |

FOREIGN PATENT DOCUMENTS

| | | |
|---|---|---|
| 390 206 | 10/1990 | European Pat. Off. . |
| 753 341 | 1/1997 | European Pat. Off. . |

*Primary Examiner*—Raj Bawa
*Attorney, Agent, or Firm*—Julie Blackburn

[57] ABSTRACT

A pigmented water-in-oil emulsion cosmetic stick composition comprising, by weight of the total composition, 0.5–50% water, 0.5–70% of a volatile solvent having a viscosity of 0.2 to 20 centipoise at 25° C., 0.5–40% of a hydrocarbon wax, and 0.5–40% of a fluorinated oil.

17 Claims, No Drawings

PIGMENTED WATER-IN-OIL EMULSION COSMETIC STICKS

RELATED APPLICATIONS

This application is a continuation of provisional patent application Ser. No. 60/065,880, filed Nov. 17, 1997.

TECHNICAL FILED

The invention is in the field of pigmented cosmetic stick compositions.

BACKGROUND OF THE INVENTION

Pigmented cosmetic stick compositions such as lipstick, eyeshadow, and concealer, are most often anhydrous. Generally, most of the ingredients which are necessary to formulate aethestically pleasing cosmetic sticks are not compatible with water. Thus, it has been difficult to formulate pigmented cosmetic sticks which contain appreciable levels of water and yet still exhibit commercially acceptable properties. Such water-containing sticks have been traditionally very unstable. In addition, lipsticks in particular, which contain appreciable amounts of water are desireable from a marketing standpoint since consumers associate water with hydration and other positive effects.

Accordingly, there is a need for stable, pigmented cosmetic sticks containing appreciable levels of water.

SUMMARY OF THE INVENTION

The invention is directed to a pigmented water-in-oil cosmetic stick composition comprising, by weight of the total composition:

0.5–50% water, 0.5–70% of a volatile solvent having a viscosity of 0.5 to 20 centipoise at 25° C.

0.5–40% of a hydrocarbon wax having a melting point of 35 to 120° C., and 0.5–20% of a fluorinated oil.

DETAILED DESCRIPTION

The term "stick" refers to cosmetic compositions having a consistency such that they can be molded into the form of a stick—for instance by being heated until molten and then poured into a mold and cooled. Also included within the definition of "stick" are compositions of the invention that are capable of being formed into sticks, but are poured into pans or other types of cake or cream forms to deliver certain consumer benefits. For example, an eyeshadow composition in accordance with the invention may be molded in the stick form, but it may be desired to pour it into a pan because this container is more desireable from a consumer standpoint.

The composition of the invention contains the following components:

THE VOLATILE SOLVENT

The composition of the invention contains 0.5–70%, preferably 1–60%, more preferably 5–50% of a volatile solvent. The volatile solvent component of the composition is a liquid at room temperature, and enables easy formulation of the cosmetic stick of the invention. The term "volatile" means that the solvent has a measureable vapor pressure, i.e. a vapor pressure of at least 2 mm. of mercury at 20° C. When the cosmetic stick product of the invention is applied to skin or lips, the volatile solvent of the invention must be capable of flashing off to leave the other ingredients in the stick on the skin. Suitable volatile solvents include linear silicones, cyclic silicones, paraffinic hydrocarbons, or mixtures thereof.

Cyclic silicones (or cyclomethicones) are of the general formula:

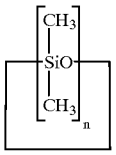

where n=3–7.

Linear volatile silicones in accordance with the invention have the general formula:

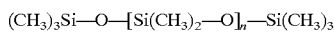

where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

Also suitable as the volatile solvent are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–190, preferably 160 to 180 and a boiling point range of 30 to 320, preferably 60–260 degrees C., and a viscosity of less than 20 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable. The preferred volatile solvent for use in the compositions of the invention is cyclomethicone.

THE HYDROCARBON WAX

The cosmetic stick compositions of the invention contain 0.5–40%, preferably 1–35%, more preferably 3–25% by weight of the total composition of a hydrocarbon wax having a melting point of 30 to 135° C. Preferably, the hydrcarbon wax is an ethylene homopolymer or ethylene copolymer. The molecular weight of the ethylene homopolymer and/or copolymers used as the wax component may vary, so long as the melting point of the homo- or copolymer either alone or in combination is not greater than 135° C. Generally polyethylene waxes having a melting point range of 30 to 135° C. will have a molecular weight ranging from about 100 to 2,000. Preferably the ethylene copolymers are comprised of ethylene monomer units in either repetitive or randon sequence, in combination with monomer units of the following formula:

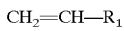

wherein $R_1$ is a $C_{1-30}$ straight or branched chain saturated or unsaturated alkyl, aryl, or aralkyl, preferably a $C_{1-10}$ straight or branched chain alkyl. Examples of ethylene homo- and copolymers which may be used in the invention are set forth in U.S. Pat. No. 5,556,613, which is hereby incorporated by reference.

Preferably, the compositions of the invention contain a was which is a homopolymer of ethylene.

THE FLUORINATED OIL

The compositions of the invention contain 0.5–20%, preferably 1–15%, more preferably 2–10% of a fluorinated oil. The fluorinated oil is preferably a liquid at room temperature, and nonvolatile, i.e. it has a vapor pressure of less than about 2 mm. of mercury at 20° C. The term "fluorinated oil" means an oil having a chemical formula wherein one or more fluorine atoms are substituted for one or more hydrogen atoms in the chemical formula of the oil.

Preferred fluorinated oils are fluorinated guerbet esters. The term "guerbet ester" means an ester which is formed by the reaction of a guerbet alcohol having the general formula:

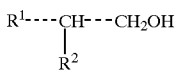

with a carboxylic acid having the general formula:

$$R^3COOH,$$

or $$HOOC—R^3—COOH$$

wherein $R^1$ and $R^2$ are each independently a $C_{4-20}$ alkyl and $R^3$ is a substituted or unsubstituted $C_{1-50}$ straight or branched chain saturated alkyl, alkylene, or phenyl, wherein the substituents are halogen, hydroxyl, carboxyl, and alkylcarbonylhydroxy. A fluoro guerbet ester is formed by the reaction of a guerbet alcohol and carboxylic acid (as defined above), and a fluoroalcohol having the following general formula:

$$CF_3—(CF_2)_n—CH_2—CH_2—OH$$

wherein n is from 3 to 40.

Examples of guerbet esters are as set forth in U.S. Pat. No. 5,488,121 which is hereby incorporated by reference. Suitable fluoro-guerbet esters are set forth in U.S. Pat. No. 5,312,968 which is hereby incorporated by reference.

Most preferred are fluoro guerbet meadowfoam esters which are prepared by the reaction of a suitable guerbet alcohol and meadowfoam fatty methyl esters or triglycerides. Meadowfoam guerbet esters are disclosed in U.S. Pat. No. 5,646,321, which is hereby incorporated by reference. Guerbet meadowfoam esters conform to the following formula:

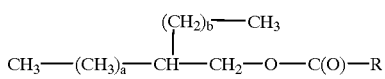

wherein R is:

60–65% by weight —(CH$_2$)$_3$—CH=CH—(CH$_2$)$_{13}$—CH$_3$

12–20% by weight of a mixture of:
(a) —(CH$_2$)$_3$—CH=CH—(CH$_2$)$_{15}$—CH$_3$, and
(b) —(CH$_2$)$_{11}$—CH=CH—(CH$_2$)$_7$—CH$_3$, and 15–28% by weight —(CH$_2$)$_3$—CH=CH—(CH$_2$)$_6$—CH=CH—(CH$_2$)$_6$—CH3 wherein a and b are each independently integers ranging from 4 to 20.

Fluoro guerbet meadowfoam esters are simply guerbet meadowfoam esters wherein one or more of the hydrogens on the ester are substituted with fluorine atoms. Most preferred is a fluoro guerbet ester having the tentative CTFA name fluoro-octyldodecyl meadowfoamate. This ester is sold by Siltech, Norcross Georgia as Developmental Ester L61125A, under the tradename Silube GME-F.

Also suitable as the fluorinated oil component are perfluoroalkanes or fluorosilicones such as trimethylsilyl endcapped fluorosilicone oils, polytrifluoropropylmethylsiloxanes, and the like.

Perfluoroalkanes have the general formula $C_nF_{2n+2}$ where n is preferably greater than 19.

Examples of fluorine modified silicone derivatives are disclosed in U.S. Pat. No. 5,548,054, which is hereby incorporated by reference. Also suitable are fluorinated silicones disclosed in U.S. Pat. No. 5,358,719, which is hereby incorporated by reference. These silicones have the following general formula:

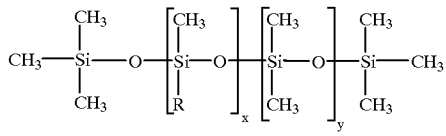

where R is —(CH$_2$)$_p$AF wherein A is a perfluoroalkyl radical having 1–30 carbon atoms, p is 1 to 10, and x and y are each independently 1–300.

Also suitable are perfluoropolyethers like those disclosed in U.S. Pat. Nos. 5,183,589, 4,803,067, 5,183,588, and 5,358,719, all of which are incorporated by reference, are also suitable. These perfluoropolyethers have the general formulas:

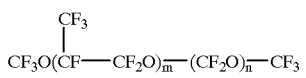

wherein the ratio of m:n is 5 to 40 respectively, or

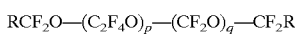

wherein the ratio of p to q is 0.5 to 1.5 respectively, and R is a fluorine atom, —COOH, —COOCH$_3$, —CH$_2$OH, —CH$_2$O—CH$_2$—CHOH—CH$_2$OH or —CH$_2$(OCH$_2$CH$_2$)$_p$—OH wherein p is 1 or 2, or

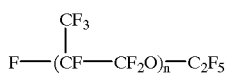

where n is 10–500, and

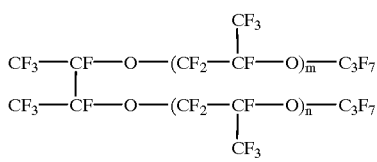

where m and n are whole numbers ranging from 0 to 3.

The above perfluoropolyethers are commercially available from Montefluos under the tradename Fomblin.

In the preferred compositions of the invention, the fluorinated oil is a fluorinated guerbet ester, in particular, fluorooctyldodecyl meadowfoamate.

PIGMENTS AND POWDERS

The cosmetic stick compositions of the invention are "pigmented", thus they contain a certain level of particulate materials which provide color when the cosmetic is applied as a film on the lips or skin. Preferably the cosmetic sticks of the invention contain 0.1–35%, more preferably 0.5–30%, most preferably 1–25% by weight of the total composition of such materials, which generally have a particle size of 0.02 to 200, preferably 0.5 to 100, microns. The particulate matter may be pigments or other powder-like particulates such as bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned particulates may be surface treated with lecithin, amino acids, mineral oil, silicone oil or various other agents either alone or in combination, which coat the powder surface and render the particles more lipophilic in nature.

The particulate materials may comprise various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors. Inorganic pigments include iron oxides, ultramarines, chromium, chromium hydroxide colors, and mixtures thereof.

Preferably the composition will contain both pigments and powder-like particulates. Obviously the ratio of pigments and powder-like particulates will depend on the type of cosmetic being formulated. Color cosmetics generally have a much higher concentration of color than other types of cosmetics. Generally the weight ratio of pigment to powder-like particulates will range from 1:50 to 50:1.

OTHER INGREDIENTS

The cosmetic sticks of the invention may contain other ingredients which provide various beneficial properties.

Nonvolatile Non-Fluorinated Oils

The composition of the invention may contain 0.01–50%, more preferably 0.1–45%, most preferably 1–40% by weight of the total composition of a nonvolatile oil in addition to the fluorinated oil. The term "nonvolatile" means that the oil has a vapor pressure of less than 2 mm. of mercury at 20° C. Preferably the oils are water insoluble, are liquids at room temperature, and have a viscosity ranging from 5 to 1,000,000, preferably 10 to 600,000 centipoise at 25° C. A variety of nonvolatile oils are suitable, including silicones, esters, lipids, and so on.

Silicones

Suitable silicones include polyalkyl siloxanes, polyaryl siloxanes, polyalkylaryl siloxanes, polyether siloxane copolymers, amine-functional silicones, and mixtures thereof. Such silicones have the following general formula:

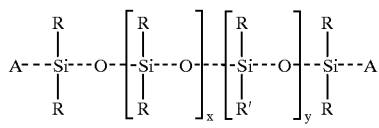

wherein R and R' are each independently $C_{1-30}$ alkyl, an aryl substitutent which is a phenyl or a phenyl ring connected to the Si by an alkylene bridge up to 3 carbons long, trimethylsiloxy, or an alkyl substituted with one or more amino groups, and x and y are each independently 0–100,000, with the proviso that x+y equals at least one and A is siloxy endcap unit. Preferred is where A is methyl, R and R' are each independently methyl, phenyl, or trimethylsiloxy. Silicones which fit this definition including dimethicone, phenyl trimethicone, diphenyl dimethicone, hexadecyl methicone, cetyl dimethicone, and so on.

Esters

Suitable nonvolatile oils for use in the compositions of the invention are esters having the general formula RCO—OR wherein each R is independently a $C_{1-25}$ straight or branched chain saturated or unsaturated alkyl, alkylcarbonyloxyalkyl, or alkoxycarbonylalkyl, aryl, which may be substituted or unsubstituted with halogen, hydroxyl, alkyl, and the like, are also suitable for use in the compositions of the invention.

Examples of suitable esters include alkyl acetates, alkyl behenates, alkyl lactates, alkyl benzoates, alkyl octanoates, alkyl salicylates, and in particular $C_{12-15}$ alkyl benzoate. Examples of further esters are set forth on pages 502–506 of the CTFA Cosmetic Ingredient Handbook, Second Edition, 1992, which is hereby incorporated by reference.

Fats and Oils

Fats and oils are also suitable as the nonvolatile oil component. These materials are generally defined as glyceryl esters of fatty acids (triglycerides), as well as the synthetically prepared esters of glycerin and fatty acids having the following general formula:

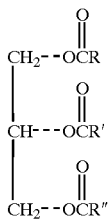

wherein R, R', and R" are each independently fatty acid radicals. Examples of such materials include oils such as apricot kernel oil, avocado oil, canola oil, olive oil, sesame oil, peanut oil, soybean oil, trilinolenin, trilinolein, trioctanoin, tristearin, triolein, sesame oil, rapeseed oil, sunflower seed oil, and so on.

Fatty Acids

Fatty acids are also suitable as the nonvolatile oil component. Fatty acids are the carboxylic acids obtained by hydrolysis of animal or vegetable fats and oils. Carboxylic acids having alkyl chains shorter than about seven carbon atoms are not generally considered fatty acids. Fatty acids have the general structure R—COOH where R is a straight or branched chain saturated or unsaturated $C_{7-65}$ alkyl. Examples of suitable fatty acids include arachidic acid, arachidonic acid, behenic acid, capric acid, caproic acid, caprylic acid, coconut acid, corn acid, cottonseed acid, hydrogenated coconut acid, hydroxystearic acid, lauric acid, linoleic acid, linolenic acid, linseed acid, myristic acid, oleic acid, palmitic acid, palm kernel acid, soy acid, tallow acid, and the like.

Fatty Alcohols

Fatty alcohols may also be used as the nonvolatile oil. Fatty alcohols are generally made by reducing the fatty acid —COOH group to the hydroxyl function. They generally have the formula $RCH_2OH$. Examples of fatty alcohols are behenyl alcohol, $C_{9-11}$ alcohol, $C_{12-13}$ alcohol, $C_{12-15}$ alcohol, $C_{12-16}$ alcohol, caprylic alcohol, cetearyl alcohol, cetyl alcohol, coconut alcohol, decyl alcohol, lauryl alcohol, myristyl alcohol, oleyl alcohol, and the like.

Hydrocarbons

Nonvolatile hydrocarbons are also suitable for use as the nonvolatile oil. Examples of suitable hydrocarbons include $C_{20-60}$ isoparaffins, hydrogenated polyisobutene, mineral oil, mineral spirits, squalene, paraffin, petrolatum, petroleum distillates, squalene, squalane, polyethylene, polydecene, and mixtures thereof. Preferred hydrocarbons are polydecene, squalane, and squalene.

Lanolin and Lanolin Derivatives

Also suitable as the nonvolatile oil are lanolin and derivatives thereof which are liquid at room temperature. Examples of such materials include acetylated hydrogenated lanolin, acetylated lanolin alcohol, laneth, lanolin acid, lanolin oil, lanolin alcohol, and so on.

The preferred compositions of the invention contain 0.01–50% by weight of the total composition of a nonvolatile nonfluorinated oil which is a liquid at room temperature, preferably squalene, squalane, polydecene, glycolipids, and mixtures thereof.

Silicone Film Formers

It may be desired to add silicone film formers to the compositions of the invention to improve adherence to skin, transfer resistance, and other characteristics. If such film formers are added, about 0.01–20%, preferably 0.05–15%, more preferably 0.1–10% by weight of the total composition of silicone film formers are added. Alkyl- or arylsiloxy silicate polymers having the following formula are good silicone film formers:

$$[(RR'R'')_3SiO_{1/2}]_x[SiO_2]_y$$

wherein R, R' and R" are each independently a $C_{1-10}$ straight or branched chain alkyl or phenyl, and x and y are such that the ratio of $(RR'R'')_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2-0749 and 2-0747, which is a blend of about 40–60% volatile silicone and 40–60% trimethylsiloxy silicate. Dow Corning 2-0749 in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41.

Preferred silicone film formers are silicone ester waxes comprising units of the general formula $R_a R^E_b SiO_{[4-(a+b)]/2]}$ or $R^{13}_x R^E_y SiO_{1/2}$, wherein R and $R^{13}$ are each independently an organic radical such as alkyl, cycloalkyl, or aryl, or, for example, methyl, ethyl, propyl, hexyl, octyl, decyl, aryl, cyclohexyl, and the like, a is a number ranging from 0 to 3, b is a number ranging from 0 to 3, a+b is a number ranging from 1 to 3, x is a number from 0 to 3, y is a number from 0 to 3 and the sum of x+y is 3, and wherein $R^E$ is a carboxylic ester containing radical. Preferred $R_E$ radicals are those wherein the ester group is formed of one or more fatty acid moieties (e.g. of about 2, often about 3 to 10 carbon atoms) and one or more aliphatic alcohol moieties (e.g. of about 10 to 30 carbon atoms). Examples of such acid moieties include those derived from branched-chain fatty acids such as isostearic, or straight chain fatty acids such as behenic. Examples of suitable alcohol moieties include those derived from monohydric or polyhydric alcohols, e.g. normal alkanols such as n-propanol and branched-chain etheralkanols such as (3,3,3-trimethylolpropoxy)propane. Preferably the ester subgroup (i.e. the carbonyloxy radical) will be linked to the silicon atom by a divalent aliphatic chain that is at least 2 or 3 carbon atoms in length, e.g. an alkylene group or a divalent alkyl ether group. Most preferably that chain will be part of the alcohol moiety, not the acid moiety.

Preferably the silicone ester will have a melting point of no higher than about 90° C. It can be a liquid or solid at room temperature. Preferably it will have a waxy feel and a molecular weight of no more than about 100,000 daltons.

Silicone esters having the above formula are disclosed in U.S. Pat. Nos. 4,725,658 and 5,334,737, which are hereby incorporated by reference. Preferred silicone esters are the liquid siloxy silicates disclosed in U.S. Pat. No. 5,334,737, e.g. diisostearoyl trimethylolpropane siloxy silicate (prepared in Examples 9 and 14 of this patent), and dilauroyl trimethylolpropane siloxy silicate (prepared in Example 5 of the patent), which are commercially available from General Electric under the tradenames SF 1318 and SF 1312, respectively.

Shine Enhancing Polymers

It may be desireable to include other ingredients in the formulation, in particular certain ingredients which enhance shine of the finish provided by the cosmetic composition of the invention. About 0.1–25%, preferably 0.5–15%, more preferably 1–10% of shine enhancers are suggested. Examples of shine enhancing ingredients are homo- or copolymers which are clear, or in other words have an index of refraction of 1.5 or greater. Examples of clear polymers are alkylated polyvinylpyrrolidones sold by International Specialty Products under the GANEX tradename. These polymers are copolymers of vinylpyrrolidone and long chain alpha olefins, and have the following general formula:

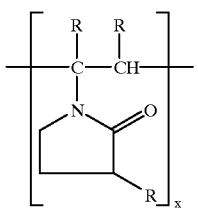

wherein R is H or a $C_{1-40}$ straight or branched chain alkyl, preferably a $C_{6-22}$ straight or branched chain alkyl. Examples of such polymers are disclosed in U.S. Pat. Nos. 4,514,271, 3,423,381, 3,423,381, and 3,417,054, all of which are hereby incorporated by reference. The composition preferably comprises 0.5–35%, preferably 1–20%, more preferably 1–15% of a $C_{6-22}$ alkylated polyvinylpyrrolidone. Particularly preferred are PVP/eicosene copolymer and PVP/hexadecene copolymer, and in particular PVP/eicosene copolymer.

Also suitable are polyvinylpyrrolidone (PVP) homopolymers, which may be purchased from International Special Products under the PVP-K tradename, in particular PVP K-15, PVP K-30, PVP K-60, PVP K-90, PVP K-120.

PVP/acetate copolymers, which are copolymers of vinylpyrrolidone and vinylacetate, are also suitable shine enhancers. Such polymers are sold under the PVP/VA tradename by International Specialty Products.

Also suitable shine enhancers are monoalkyl esters of poly(methylvinyl ether/maleic acid), which are sold by International Specialty Products under the GANTREZ tradename.

Organosiloxane Emulsifiers

The composition of the invention preferably comprises 0.1–40%, more preferably 0.5–20%, and most preferably 1–15% of the polymeric organosiloxane emulsifier containing at least one lipophilic radical or portion and at least one hydrophilic radical or portion. Organosiloxane emulsifiers suitable for use in the compositions of the invention can be identified as those which, when combined with organic and inorganic pigments, and incorporated into an anhydrous stick composition provide a homogeneous single phase product. The polymeric organosiloxane used in the invention may be a liquid or solid at room temperature. The polymeric organosiloxane is generally a water-in-oil or oil-in-water type surfactant which is preferably nonionic, having an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

$$HLB = 7 + 11.7 \times \log M_w/M_o$$

where $M_w$ is the molecular weight of the hydrophilic group portion and $M_o$ is the molecular weight of the lipophilic group portion.

The term "organosiloxane polymer" means a polymer containing a polymeric backbone including repeating siloxy units that may have cyclic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxy-polypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, sulfonates, sulfates, phosphates, or amines.

The term "lipophilic radical" means an organic radical that, when substituted onto the organosiloxane polymer backbone, confers lipophilic properties to the substituted portion of the polymer. Examples of organic radicals which will conver lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof. The $C_{1-40}$ alkyl may be non-interrupted, or interrupted by one or more oxygen atoms, a benzene ring, amides, esters, or other functional groups.

The polymeric organosiloxane emulsifier used in the invention may have any of the following general formulas:

or

or

wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof. T is a trifunctional siloxy unit having the empirical formula $RR'SiO_{1.5}$ or $RRSiO_{1.5}$. Q is a quadrifunctional siloxy unit having the empirical formula $SiO_2$, and D, D', D", x, y, and z are as set forth below, with the proviso that the compound contains at least one hydrophilic radical and at least one lipophilic radical. Examples of emulsifiers used in the compositions of the invention are of the general formula:

$$MD_xD'_yD''_zM$$

wherein the trimethylsiloxy endcap unit is unsubstituted or mono-substituted, wherein one methyl group is substituted with a lipophilic radical or a hydrophilic radical. Examples of such substituted trimethylsiloxy endcap units include $(CH_3)_2HPSiO$, $(CH_3)_2LPSiO$, $(CH_3)_2CH_2HPSiO$, $(CH_3)_2CH_2LPSiO$, wherein HP is a hydrophilic radical and LP is a lipophilic radical. D, D', and D" are difunctional siloxy units substituted with methyl, hydrogen, a lipophilic radical, a hydrophilic radical or mixtures thereof. In this general formula:

x=0–5000, preferably 1–1000 y=0–5000, preferably 1–1000, and z=0–5000, preferably 0–1000, with the proviso that the compound contains at least one lipophilic radical and at least one hydrophilic radical. Examples of these polymers are disclosed in U.S. Pat. No. 4,698,178, which is hereby incorporated by reference.

Particularly preferred is a linear silicone of the formula:

$$MD_xD'_yD''_zM$$

wherein $M=RRRSiO_{1/2}$

D and $D'=RR'SiO_{2/2}$ $D''=RRSiO_{2/2}$ x, y, and z are each independently 0–1000, where R is methyl or hydrogen, and R' is a hydrophilic radical or a lipophilic radical, with the proviso that the compound contains at least one hydrophilic radical and at least one lipophilic radical.

Most preferred is wherein

M=trimethylsiloxy $D=Si[(CH_3)][(CH_2)_nCH_3]O_{2/2}$ where n=1–40, $D'=Si[(CH_3)][(CH_2)_o-O-PE)]O_{2/2}$ where PE is $(-C_2H_4O)_a(-C_3H_6O)_bH$, o=0–40, a=1–100 and b=1–100, and $D''=Si(CH_3)_2O_{2/2}$ Typical examples of preferred organosiloxane emulsifiers in accordance with the invention include those set forth below:

I.

II.

III.

IV.

V.

wherein LP is a lipophilic radical

HP is a hydrophilic radical x is 0–5000 y is 0–5000, and z is 0–5000, with the proviso that the organosiloxane contains at least on hydrophilic radical and at least one lipophilic radical.

More preferred are compounds of the generic formula I wherein LP is a lipophilic radical which is a $C_{1-40}$ straight or branched chain alkyl, HP is a hydrophilic radical containing hydroxy-polyethyleneoxy, and z is at least 1. Most preferred is a compound of the formula:

wherein p is 10–40, preferably 12–20, most preferably 15, and PE is $(-C_2H_4O)_a(-C_3H_6O)_b-H$ where x, y, z, a, and b are such that the maximum molecular weight of the polymer is approximately 50,000. Organosiloxane polymers useful in the compositions of the invention are commercially available from Goldschmidt Corporation under the ABIL tradename. The preferred polymer is cetyl dimethicone copolyol and has the tradename ABIL WE 09 or ABIL WS 08. The cetyl dimethicone copolyol may be used alone or in conjunction with other non-silicone organic emulsifiers. Preferred is where the cetyl dimethicone copolyol is in an admixture with other non-silicone organic emulsifiers and emollients. In particular, blends of 25–50% of the organosiloxane emulsifier, 25–50% of a non-silicone organic emulsifier, and 25–50% by weight emollients or oils are preferred. For example, the mixtures identified by the C.T.F.A. names cetyl dimethicone copolyol (and) polyglyceryl 4-isostearate (and) hexyl laurate, or cetyl dimethicone copolyol (and) polyglyceryl-3 oleate (and) hexyl laurate both work well. These blends contain approximately 25–50% of each ingredient, for example ABIL WE 09 contains approximately, by weight of the total ABIL composition, 25–50% cetyl dimethicone copolyol, 25–50%, polyglyceryl 4-isostearate, and 25–50% of hexyl laurate which is an emollient or oil. In particular, the mixture of cetyl dimethicone copolyol/polyglyceryl-4-isostearate/hexyl laurate sold by Goldschmidt & Co. under the tradename ABIL WE 09 contains 33% by weight of the total blend of cetyl dimethicone copolyol, 34% by weight of the total blend of polyglyceryl-4-isostearate, and 33% by weight of the total blend of hexyl laurate.

Another type of preferred organosiloxane emulsifier suitable for use in the compositions of the invention are emulsifiers sold by Union Carbide under the Silwet™ trademark. These emulsifiers are represented by the following generic formulas:

$(Me_3Si)_{y-2}[(OSiMe_2)_{x/y}O\text{-}PE]_y$ wherein $PE = -(EO)_m(PO)_nR$

R=lower alkyl or hydrogen

Me=methyl

EO is polyethyleneoxy

PO is polypropyleneoxy m and n are each independently 1–5000 x and y are each independently 0–5000, and

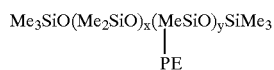

$Me_3SiO(Me_2SiO)_x(MeSiO)_ySiMe_3$ | PE wherein $PE = -CH_2CH_2CH_2O(EO)_m(PO)_nZ$ Z=lower alkyl or hydrogen, and Me, m, n, x, y, EO and PO are as described above, with the proviso that the molecule contains a lipophilic portion and a hydrophilic portion. Again, the lipophilic portion can be supplied by a sufficient number of methyl groups on the polymer backbone.

Particularly preferred is a Silwet™ polymer of the following general formula:

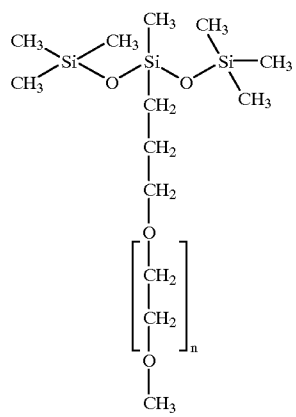

wherein n is 1–10, preferably 8.

Another preferred organosiloxane emulsifier for use in the compositions of the invention is dimethicone copolyol.

Examples of other polymeric organosiloxane surfactants or emulsifiers include amino/polyoxyalkyleneated polydiorganosiloxanes disclosed in U.S. Pat. No. 5,147,578. Also suitable are organosiloxanes sold by Goldschmidt under the ABIL trademark including ABIL B-9806, as well as those sold by Rhone-Poulenc under the Alkasil tradename. Also, organosiloxane emulsifiers sold by Dow Corning, such as Dow Corning 3225C Formulation Aid, Dow Corning 190 Surfactant, Dow Corning 193 Surfactant, Dow Corning Q2-5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention.

Particularly preferred are pigmented water-in-oil emulsion lipstick compositions comprising, by weight of the total composition:

5–50% cyclomethicone,

3–25% of a hydrocarbon wax which is an ethylene homopolymer, or a copolymer of ethylene and a monomer unit of the formula:

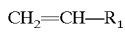

$CH_2=CH-R_1$ wherein $R_1$ is a $C_{1-30}$ straight or branched chain saturated or unsaturated alkyl, aryl, or aralkyl, 2–20% of a nonvolatile fluorinated oil, 1–20% of particulate materials having a particle size of 0.02 to 100 microns, wherein the particulate materials are a mixture of pigments and powder-like particulates in a ratio of 1:50 to 50:1, 1–40% of a nonvolatile oil which is a hydrocarbon, ester, or mixtures thereof.

0.1–10% of a silicone film former, and

1–10% of a shine enhancer which is a homo- or copolymer which has an of refraction of 1.5 or greater.

The invention will be further described in connection with the following examples which are set forth for the purposes of illustration only.

EXAMPLE 1

Pigmented, water-in-oil emulsion cosmetic sticks were made according to the following formula:

|  | w/w % | | |
| --- | --- | --- | --- |
|  | 1 | 2 | 3 |
| PVP/eicosene copolymer | 3.90 | 3.90 | 3.90 |
| Polydecene | 4.60 | 4.60 | 4.60 |
| Fluoro octyldodecyl meadowfoamate | 6.50 | 6.50 | 6.50 |
| Synthetic wax | 13.00 | 13.00 | 11.30 |
| Ozokerite | 1.35 | 1.35 | 1.10 |
| Ceresin | 1.50 | 1.50 | 1.35 |
| Vitamin E acetate | 0.10 | 0.10 | 0.10 |
| Aloe extract | 0.30 | 0.30 | 0.30 |
| Squalene/glycolipids | 17.57 | 7.57 | 9.67 |
| Propylparaben | 0.10 | 0.10 | 0.10 |
| BHA | 0.10 | 0.10 | 0.10 |
| Diisostearoyl trimethylolpropane siloxy silicate | 1.00 | 1.00 | 1.00 |
| Pentaerythrityl tetraoctanoate | 1.50 | 1.50 | 1.50 |
| Cetyl dimethicone copolyol/glyceryl -4-isostearate/hexyl laurate* | 3.48 | 3.48 | 3.48 |
| D&C Red 7 calcium lake | 10.00 | 10.00 | 10.00 |
| Mica, silica | 5.00 | 5.00 | 5.00 |
| Cyclomethicone | 15.00 | 25.00 | 15.00 |
| Water | 15.00 | 15.00 | 25.00 |

*A mixture of 33% by weight cetyl dimethicone copolyol, 34% by weight polyglyceryl-4-isostearate, and 33% by weight hexyl laurate.

The compositions were made by first roller milling the pigments in the oils. Next, the waxes were melted and the oils and other ingredients were added. The water was added and emulsified into the composition. The molten product was poured into stick molds and allowed to cool.

We claim:

1. A pigmented water-in-oil emulsion cosmetic stick composition comprising, by weight of the total composition:

0.5–50% water, 0.5–70% of a volatile solvent having a viscosity of 0.2 to 20 centipoise at 25° C., selected from the group consisting of:

(a) cyclic silicone of the formula;

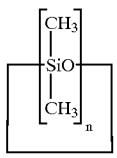

where n=3–7;
(b) a linear silicone of the formula $(CH_3)_3Si-O-[Si(CH_3)_2-O]_n-Si(CH_3)_3$
where n=0–7;
(c) a straight or branched chain paraffinic hydrocarbon having 5 to 40 carbon atoms,
(d) or mixtures thereof,
0.5–40% of a hydrocarbon wax having a melting point of 30 to 135° C. selected from the group consisting of:
(a) an ethylene homopolymer,
(b) a copolymer of ethylene and a monomer having the formula:

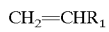

wherein $R_1$ is a $C_{1-30}$ straight or branch chain saturated or unsaturated alkyl, aryl, or aralkyl, and
(c) mixtures thereof; and
0.5–40% of a fluorinated oil selected from the group consisting of:
(a) a fluorinated guerbet ester,
(b) a fluorinated guerbet meadowfoam ester prepared by the reaction of a fluoropguerbet alcohol and meadowfoam fatty methyl esters or triglycerides,
(c) a perfluoroalkane having the general formula $C_nF_{2n+2}$ where n is greater than 19,
(d) a fluorinated silicone having the formula:

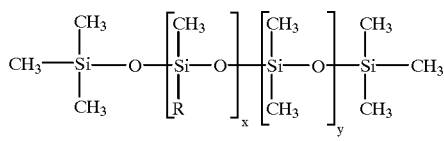

where R is $-(CH_2)_pAF$ wherein A is a perfluoroalkyl radical having 1 30 carbon atoms p is 1 to 10, and x and y are each independently 1–300, (e) a perfluoropolyether; and
(f) mixtures thereof.

2. The composition of claim 1 wherein the volatile solvent is cyclomethicone.

3. The composition of claim 1 wherein the hydrocarbon wax is an ethylene homopolymer.

4. The composition of claim 1 wherein the fluorinated oil is a fluorinated guerbet ester.

5. The composition of claim 1 wherein the fluorinated oil is a fluorinated guerbet meadowfoam ester.

6. The composition of claim 5 wherein the fluorinated guerbet meadowfoam ester is fluoro octyldodecyl meadowfoamate.

7. The composition of claim 1 further containing 0.1–35% by weight of the total composition of pigment.

8. The composition of claim 7 wherein the pigment is an inorganic pigment, an organic pigment, or mixtures thereof.

9. The composition of claim 8 wherein the inorganic pigment is iron oxides, and the organic pigments are D&C or FD&C colors.

10. The composition of claim 1 further comprising 1–40% by weight of the total composition of a non-volatile, non-fluorinated oil.

11. The composition of claim 10 wherein the non-volatile non-fluorinated oil is an ester, a hydrocarbon, or mixtures thereof.

12. The composition of claim 1 further comprising 0.01–15% by weight of the total composition of an organosiloxane emulsifier.

13. The composition of claim 12 wherein the organosiloxane emulsifier is non-ionic.

14. The composition of claim 13 wherein the organosiloxane emulsifier has an HLB of 2 to 12.

15. The composition of claim 14 wherein the surfactant is a mixture of an organosiloxane surfactant and a non-ionic surfactant.

16. The composition of claim 15 wherein the surfactant is a mixture of cetyl dimethicone copolyol, and hexyl laurate, and polyglyceryl-4-isostearate.

17. The composition of claim 1 further comprising 0.01–20% by weight of the total composition of a silicone film-former.

* * * * *